United States Patent [19]
Yang

[11] Patent Number: 5,105,133
[45] Date of Patent: Apr. 14, 1992

[54] MULTIPLE MODE PERFUMER

[76] Inventor: Tai-Her Yang, 5-1 Taipin St., Su-Hu Town, Dzan-Hwa, Taiwan

[21] Appl. No.: 583,237

[22] Filed: Sep. 14, 1990

[51] Int. Cl.$^5$ ............................................. A61L 9/04
[52] U.S. Cl. .................................... 318/443; 318/445; 318/480; 422/116; 422/124
[58] Field of Search ............... 318/443, 444, 445, 446, 318/480, 558; 422/105, 116, 120, 123, 124, 305, 306; 239/63, 64, 67, 69, 70, 34, 53, 54, 55, 60, 93, 99, 380

[56] References Cited

U.S. PATENT DOCUMENTS

| | | | |
|---|---|---|---|
| 3,418,068 | 12/1968 | Gilbertson | 422/124 X |
| 3,990,848 | 11/1976 | Corris | 422/116 X |
| 3,993,444 | 11/1976 | Brown | 422/124 X |
| 4,078,891 | 3/1978 | Madjar | 422/124 X |
| 4,111,655 | 9/1978 | Quincey | 422/124 |
| 4,166,087 | 8/1979 | Cline et al. | 239/60 X |
| 4,370,300 | 1/1983 | Mori et al. | 422/105 X |
| 4,568,521 | 2/1986 | Spector | 422/105 X |
| 4,695,435 | 9/1987 | Spector | 422/124 |
| 4,707,338 | 11/1987 | Spector | 422/124 |
| 4,830,791 | 5/1989 | Muderlak et al. | 422/124 X |
| 4,903,583 | 2/1990 | Frazier | 422/306 X |
| 5,038,972 | 8/1991 | Muderlak et al. | 222/25 |

*Primary Examiner*—Bentsu Ro
*Attorney, Agent, or Firm*—Leonard Bloom

[57] ABSTRACT

An automatic perfumer capable of operating in one of a plurality of modes to suite varying room conditions, the modes including an intermittent mode for perfuming at predetermined intervals, and a light-activated intermittent mode for operating as described above and only upon the application of light, thereby avoiding needless nighttime operation.

14 Claims, 1 Drawing Sheet

5,105,133

MULTIPLE MODE PERFUMER

BACKGROUND OF THE INVENTION

1. Field of the invention

The present invention relates to automatic perfumers for improving the surrounding air quality, and more particularly, to an intermittent perfumer capable of operating in one of a plurality of modes, including continuous mode, intermittent mode, and light-activated intermittent mode.

2. Description of the Background

Conventional automatic perfumers are operated continuously, and the continuous operation leads to a number of problems. Specifically, continuously sprinkled perfume accumulates in the air in dense concentrations, which is apt to make people in the room lose their sensitivity to the scent. Moreover, continuous operation results in a waste of power and perfume in the long run.

SUMMARY OF THE INVENTION

It is, therefore, an object of the present invention to provide a perfumer capable of operating in one of a plurality of modes to suit varying room conditions.

It is another object of the present invention to provide an intermittent perfumer which can be activated by the application of light to avoid needless nighttime operation.

According to the present invention, the above-described and other objects are accomplished by providing an automatic air perfumer having a plurality of operating modes for dispersing perfume. The perfumer comprises a source of power, a mode select switch connected to the source of power and having multiple positions, and a motor for driving a blower to disperse perfume. The mode select switch has a first position in which the power is applied directly to the motor for continuous driving. The perfumer also has a timing control circuit for generating an intermittent timing signal. The mode select switch has a second position in which power is applied to the motor in accordance with the timing control signal for intermittent driving. The perfumer also has a photo-electric means for detecting light. The mode select switch has a third position in which power is applied to the motor when the photo-electric means detects light, the power then being applied in accordance with the timing control signal for intermittent driving.

BRIEF DESCRIPTION OF THE DRAWINGS

Other objects, features and advantages of the present invention will become more apparent from the following detailed description of preferred embodiments and certain modifications thereof when taken together with the accompanying drawings, in which.

DETAILED DESCRIPTION OF THE PREFERRED EMBODIMENT

Figure 1:
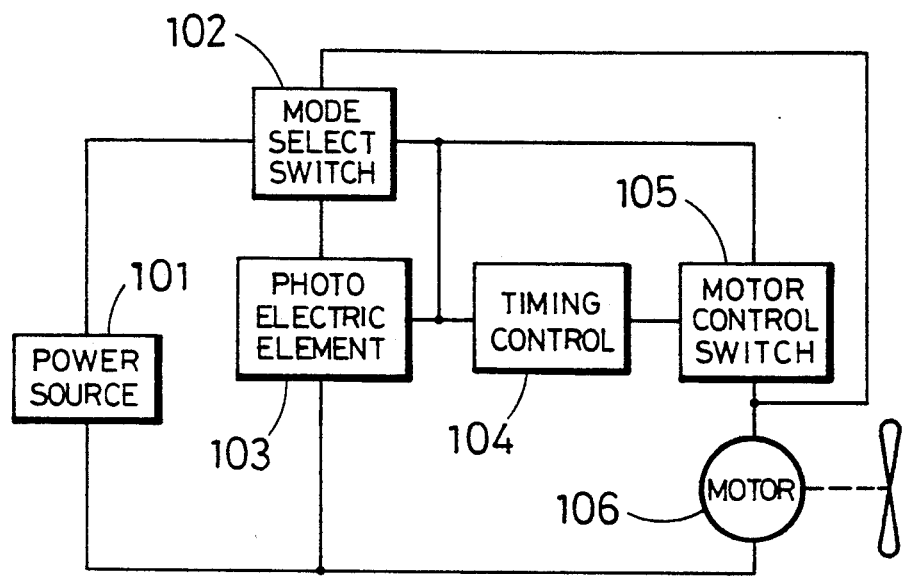
FIG. 1 is a block circuit diagram of the multiple mode perfumer according to the present invention.

FIG. 1 shows a block circuit diagram of a multiple mode perfumer according to the present invention. The multiple mode perfumer of FIG. 1 includes a conventional power source 101 and a mode select switch 102 for controlling the application of power from power source 101. As shown, mode select switch 102 preferably has a single-pole connected to power source 101, and at least four terminals, three of which correspond to three modes of operation of the perfumer. A first terminal of switch 102 corresponds to the "OFF" position. The "OFF" terminal is left unconnected.

A second terminal of switch 10 corresponds to "CONTINUOUS MODE" operation in which the perfumer emits a continuous flow of perfume. The "CONTINUOUS MODE" terminal is connected directly to a conventional motor 106 which drives a blower. As in the prior art perfumers, a supply of perfume is positioned in the airstream of the blower, and when motor 106 is activated, the perfume is gradually discharged into the surrounding airspace. When the mode switch 102 is positioned at the "CONTINUOUS MODE" terminal, power is continuously applied to motor 106 and perfume is continuously discharged.

A third terminal of switch 102 corresponds to "INTERMITTENT MODE" operation in which the perfumer emits an intermittent flow of perfume. The "INTERMITTENT MODE" terminal is connected to a timing control circuit 104, which is in turn connected to a motor control switch 105. The "INTERMITTENT MODE" terminal is also connected directly to the motor control switch 105, which is in turn connected to the motor 106. When mode switch 102 is positioned at the "INTERMITTENT MODE" terminal, the timing control circuit 104 provides an intermittent output signal to motor control switch 105 which gates power through to motor 106. Motor 106 is driven to discharge perfume according to an intermittent schedule.

A fourth terminal of switch 102 corresponds to "LIGHT-ACTIVATED INTERMITTENT MODE" operation in which the perfumer operates in the above-described intermittent mode only upon the application of light. The "LIGHT-ACTIVATED INTERMITTENT MODE" avoids the wasted operation which would otherwise occur at night. The "LIGHT-ACTIVATED INTERMITTENT MODE" terminal is connected to a photoelectric element 103, which is in turn connected through timing control circuit 104 to motor control switch 105. The "LIGHT-ACTIVATED INTERMITTENT MODE" terminal is also coupled directly to the motor control switch 105, which is in turn connected to the motor 106. When mode switch 102 is positioned at the "LIGHT-ACTIVATED INTERMITTENT MODE" terminal, the photoelectric element 103 disables the timing control circuit 104 until a predetermined intensity of light is detected at photoelectric element 103. The motor control switch 105 will not apply power to motor 106 as long as timing control circuit 104 remains disabled. However, when light is applied, photoelectric element 103 enables the timing control circuit 104, which in turn provides its intermittent output signal to motor control switch 105. Motor 106 is driven to discharge perfume according to an intermittent schedule.

Figure 2:
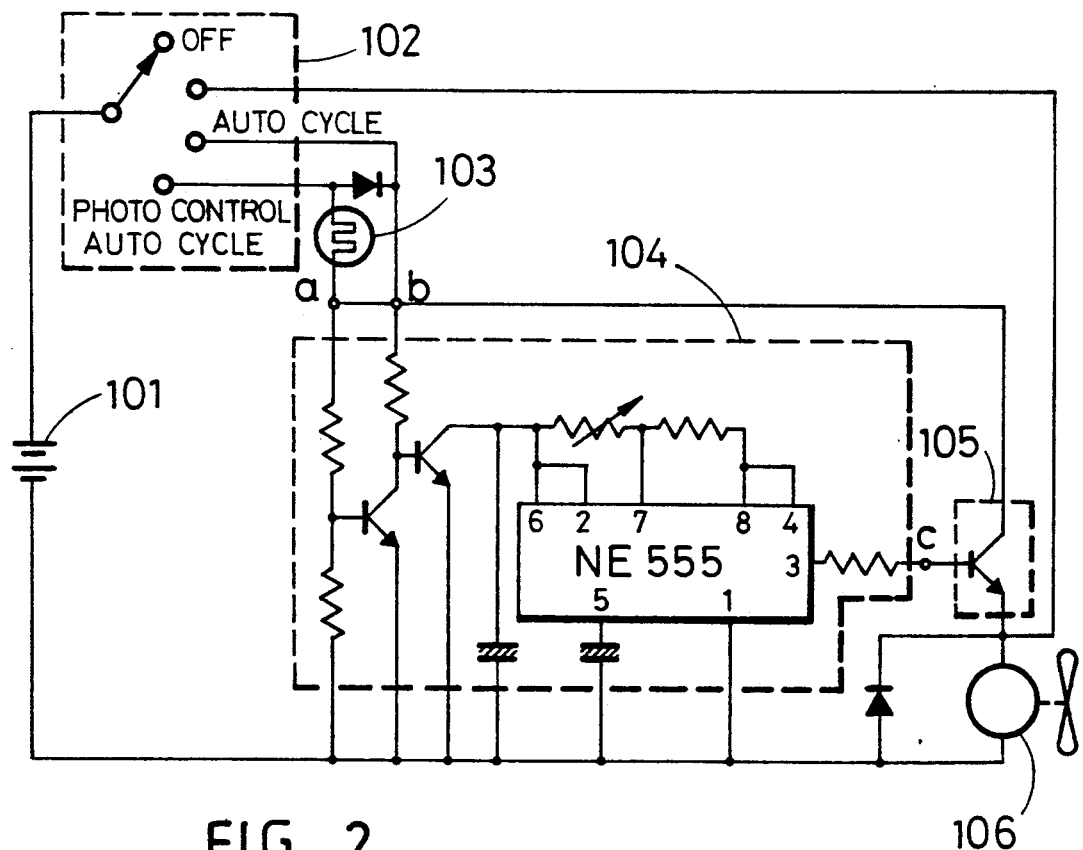
FIG. 2 is a detailed circuit diagram illustrating a preferred embodiment of the invention of FIG. 1.

FIG. 2 is a detailed schematic diagram of a preferred circuit for carrying out the above-described invention. The circuit of FIG. 2 includes a single-pole three-terminal mode select switch 102 which may be a conventional rotary switch. The single-pole of mode select switch 102 is connected to power source 101. The first terminal of switch 102 is left unconnected. The second terminal of switch 102 is connected directly to a conventional motor 106 which drives the perfume blower. The third terminal of switch 102 is connected directly to both of two input terminals a and b which enable timing control circuit 104.

Voltage must be applied to both of terminals a and b in order to enable timing control circuit 104. The dual enable is accomplished by a pair of cascaded transistors having their bases connected to terminals a and b, respectively.

Timing control circuit 104 is mainly comprised of a variable pulse generator such as an NE555 configured as shown to emit an intermittent timing signal at the desired frequency of perfuming. The output terminal c of the timing control circuit is coupled to the base of motor control switch 105, motor control switch 105 being a standard power transistor. The collector of motor control switch 105 is connected directly to the "INTERMITTENT MODE" terminal of switch 102.

The fourth terminal of switch 102 is connected through a diode to input terminal a of timing control circuit 104, and to the collector of motor control switch 105. The fourth terminal of switch 102 is also connected through photoelectric element 103 to input terminal b of timing control circuit 104. photoelectric element 103 is shown to be a conventional cadmium sulfide (CdS) photo-resistive element. However, photoelectric element 103 may alternatively be a photo-diode, phototransistor, or any other light sensitive component. In the dark, photoelectric element 103 obstructs the application of power to input terminal b of timing control circuit 104. Hence, timing control circuit 104 disables motor control switch 105 and motor 106. Conversely, a light applied to photoelectric element 103 will induce the application of power to input terminal b of timing control circuit 104, and timing control circuit 104 will intermittently enable motor control switch 105, thereby driving the motor 106 to emit perfume intermittently.

Having now fully set forth the preferred embodiments and certain modifications of the concept underlying the present invention, various other embodiments as well as certain variations and modifications of the embodiment herein shown and described will obviously occur to those skilled in the art upon becoming familiar with said underlying concept. It is to be understood, therefore, that within the scope of the appended claims, the invention may be practiced otherwise than as specifically set forth herein.

I claim:

1. An automatic air perfumer having a plurality of operating modes for dispersing perfume, said perfumer comprising:
   a source of power;
   a mode select switch connected to said source of power and having at least three positions;
   a motor for driving a blower, said mode select switch having a first position in which said power is applied directly to said motor for continuous driving thereof;
   a timing control circuit for generating an intermittent timing signal, said mode select switch having a second position in which said power is applied to said motor in accordance with said intermittent timing signal for intermittent driving thereof; and
   photo-electric means connected in series with said timing control circuit for detecting light, said mode select switch having a third position in which said power is applied to said motor when said photo-electric means detects light to activate said timing control circuit, said power thereupon being applied in accordance with said intermittent timing signal for intermittent driving thereof.

2. The air perfumer according to claim 1, wherein said photo-electric means is a photoresistive cell.

3. The air perfumer according to claim 2, wherein said photo-resistive cell is a cadmium sulfide (CdS) element.

4. The air perfumer according to claim 1, wherein said photo-electric means is a photo-diode.

5. The air perfumer according to claim 1, wherein said photo-electric means is a photo-transistor.

6. The air perfumer according to claim 1, wherein said photo-electric means is a light activated thyristor.

7. The air perfumer according to claim 1, wherein said mode select switch has four positions including a fourth "off" position in which said power is disconnected from said motor.

8. An automatic air perfumer having a plurality of operating modes for dispersing perfume, said perfumer comprising:
   a power supply;
   a mode select switch having a pole connected to said power supply and at least three throw positions;
   a motor for driving a blower, said mode select switch having a first throw position in which said power supply is connected directly to said motor for continuous driving thereof;
   a timing control circuit for generating an intermittent timing signal when activated by said mode select switch;
   a gate having a first terminal, a second terminal connected to said motor, and a gate control input connected to an output of said timing control circuit for intermittently connecting said first terminal to said second terminal in accordance with said intermittent timing signal, said mode select switch having a second throw position in which said power supply is connected directly to said first gate terminal, and said timing control circuit applies said power supply to said motor in accordance with said intermittent timing signal for intermittent driving thereof; and
   photo-electric means connected to said timing control circuit for disabling said timing control circuit for lack of light, said mode select switch having a third throw position in which said power supply is applied to said first gate terminal, and light causes said photo-electric means to enable said timing control circuit to apply said power supply to said motor in accordance with said timing control signal for intermittent driving thereof, and a lack of light causes said photo-electric means to disable said timing control circuit and open said gate.

9. The air perfumer according to claim 8, wherein said photo-electric means is a photo-resistive cell.

10. The air perfumer according to claim 9, wherein said photo-resistive cell is a cadmium sulfide (CdS) element.

11. The air perfumer according to claim 8, wherein said photo-electric means is a photo-diode.

12. The air perfumer according to claim 8, wherein said photo-electric means is a photo-transistor.

13. The air perfumer according to claim 8, wherein said photo-electric means is a light activated thyristor.

14. The air perfumer according to claim 8, wherein said mode select switch has four throw positions including a fourth "off" position in which said power is disconnected from said motor.

* * * * *